US007329535B2

(12) United States Patent
Oh et al.

(10) Patent No.: US 7,329,535 B2
(45) Date of Patent: Feb. 12, 2008

(54) APPARATUS FOR CIRCULATING CARRIER FLUID

(75) Inventors: Kwang-wook Oh, Gyeonggi-do (KR); Geun-bae Lim, Gyeonggi-do (KR); Young-sun Lee, Gyeonggi-do (KR); Yoon-kyoung Cho, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 578 days.

(21) Appl. No.: 10/292,012

(22) Filed: Nov. 11, 2002

(65) Prior Publication Data

US 2003/0092172 A1 May 15, 2003

(30) Foreign Application Priority Data

Nov. 10, 2001 (KR) .............................. 2001-69955

(51) Int. Cl.
*C12M 1/34* (2006.01)
*C12M 3/00* (2006.01)
*F16K 13/00* (2006.01)
*B01L 11/00* (2006.01)
*B32B 5/02* (2006.01)

(52) U.S. Cl. .............................. 435/287.2; 435/287.1; 435/288.5; 435/294.1; 137/252; 137/251.1; 422/103; 422/81; 422/82

(58) Field of Classification Search ............ 435/283.1, 435/286.5, 289.1, 285.1, 287.2, 288.3, 288.5, 435/287.1, 288.35, 294.1; 219/535, 201, 219/528; 392/480, 482; 165/185, 177, 182, 165/183; 422/81, 99, 102, 103, 82; 137/252, 137/251.1

See application file for complete search history.

(56) References Cited

U.S. PATENT DOCUMENTS 3,137,646 A * 6/1964 Capsuto ........................ 208/65

(Continued)

FOREIGN PATENT DOCUMENTS

CN 1248702 A 3/2000

(Continued)

OTHER PUBLICATIONS

"Intergrated System for Rapid PCR-Based DNA Analysis in Microfluidic Devices"; Authors: Julia Khandurina, Timothy E. McKnight, Stephen c. Jacobson, Larry C. Waters, Robert S. Foote, and J. Michael Ramsey; In: Analytical Chemistry, vol. 72, No. 13; American Chemical Society, Jul. 1, 2000; pp. 2995-3000.

(Continued)

*Primary Examiner*—William H. Beisner
*Assistant Examiner*—Nathan A. Bowers
(74) *Attorney, Agent, or Firm*—Cantor Colburn LLP

(57) ABSTRACT

Provided are an apparatus for circulating a carrier fluid having two or more chambers or sections, an apparatus for amplifying a nucleic acid using the same, and a chip containing the same. The apparatus for circulating a carrier fluid includes two or more chambers maintained at different temperatures, each chamber having an inlet valve containing a pneumatic air pressure port for controlling inflow of the carrier fluid to the chamber (inlet pneumatic air pressure port), and an outlet valve containing a pneumatic air pressure for controlling outflow of the carrier fluid from the chamber (outlet pneumatic air pressure port), wherein the chambers are sequentially connected such that the outlet valve of one chamber is connected to the inlet valve of an adjacent chamber in a direction the fluid flows.

12 Claims, 9 Drawing Sheets

U.S. PATENT DOCUMENTS

| | | | | | |
|---|---|---|---|---|---|
| 4,112,047 | A | * | 9/1978 | Donaldson | 423/123 |
| 4,676,274 | A | * | 6/1987 | Brown | 137/806 |
| 5,176,203 | A | * | 1/1993 | Larzul | 165/61 |
| 5,270,183 | A | | 12/1993 | Corbett et al. | 435/91.2 |
| 5,498,392 | A | * | 3/1996 | Wilding et al. | 422/68.1 |
| 5,856,174 | A | * | 1/1999 | Lipshutz et al. | 435/286.5 |
| 5,939,291 | A | | 8/1999 | Loewy et al. | 435/91.2 |
| 5,985,651 | A | | 11/1999 | Hunicke-Smith | 435/285.1 |
| 6,033,880 | A | * | 3/2000 | Haff et al. | 435/91.1 |
| 6,586,233 | B2 | * | 7/2003 | Benett et al. | 435/286.5 |
| 6,632,656 | B1 | * | 10/2003 | Thomas et al. | 435/288.5 |
| 6,680,193 | B1 | * | 1/2004 | Fouillet et al. | 435/287.2 |
| 6,911,183 | B1 | * | 6/2005 | Handique et al. | 422/102 |
| 2002/0068357 | A1 | * | 6/2002 | Mathies et al. | 435/287.2 |
| 2003/0008308 | A1 | * | 1/2003 | Enzelberger et al. | 435/6 |

FOREIGN PATENT DOCUMENTS

| | | |
|---|---|---|
| CN | 1267089 A | 9/2000 |
| JP | 58-19157 | 2/1983 |
| JP | 10-213099 | 8/1998 |
| JP | 2001-269567 | 10/2001 |
| WO | WO/00/67893 | 11/2000 |
| WO | 02/081729 A2 | 10/2002 |

OTHER PUBLICATIONS

"Microchip Module for Blood Sample Preparation and Nucleic Acid Amplification Reactions"; Authors: Po Ki Yuen, Larry J. Kricka, Paolo Fortina, Nicholas J. Panaro, Taku Sakazume, and Peter Wilding; In: Genome Research; Cold Spring Harbor Laboratory Press; 2001; pp. 405-412.

Steven A. Soper et al.; "Fabrication of Modular Microsystems for Analyzing K-RAS Mutations Using LDR"; Micro Total Analysis Systems; 2001, 459-461.

Office Action issued by The Patent Office of the People's Republic of China on Apr. 15, 2005; Re: Application No. 028033736.

* cited by examiner

APPARATUS FOR CIRCULATING CARRIER FLUID

BACKGROUND OF THE INVENTION

1. Field of the Invention

The present invention relates to an apparatus for circulating a carrier fluid. More specifically, the present invention relates to an apparatus for circulating a carrier fluid having two or more chambers or sections, an apparatus for amplifying a nucleic acid using the same, and a chip containing the same.

2. Description of the Related Art

A polymerase chain reaction (PCR) method has been developed to amplify nucleic acid sequences by being subject to a periodical hot-cold temperature cycle. In PCR, one cycle of DNA amplification requires a biochemical sample to sequentially be exposed to various temperatures, such as T1 (for denaturing)→T2 (for annealing)→T3 (for extension).

As shown in FIG. 1, a conventional PCR system has a structure where polymerase chain reaction is performed by controlling the temperatures (T1 for denaturing: 94° C., T2 for annealing: 55° C., T3 for extension: 72° C.) of a chamber retaining a biochemical fluid, such as a PCR fluid. In this system, the repetition of heating and cooling the chamber causes a time delay for heating and cooling, thus complicated circuits are needed for an accurate control of the temperatures.

U.S. Pat. No. 5,270,183 discloses an apparatus and method for the amplification of nucleic acids in a sample using the polymerase chain reaction, as shown in FIG. 2, where a polymerase chain reaction is performed by continuously flowing a biochemical fluid, such as a PCR fluid, in zigzags along different temperature zones. Therefore, this system may require an extraordinarily long channel for a biochemical fluid to follow an accurate temperature profile, because the movement from T3 section to T1 section requires passage through T2 section.

Further, as shown in FIG. 3, a PCR system is disclosed where the polymerase chain reaction is performed by continuously flowing a biochemical fluid, such as a PCR fluid, in concentric circles along different temperature zones (Proc. Miniaturized Total Analysis Systems (uTAS 2001), Louisiana State University, Steven A. Soper et al., pp. 459-461). In this system, a flow path becomes shortened as one complete cycling is repeated. Thus, the flow rate of the biochemical fluid should be accurately controlled in order to follow a temperature profile.

SUMMARY OF THE INVENTION

The present invention provides an apparatus for circulating a carrier fluid comprising a plurality of chambers or sections maintained at different temperatures and a method for operating the same. Further, the present invention provides an apparatus for amplifying a nucleic acid using and a chip comprising the apparatus.

In one aspect of the present invention, there is provided an apparatus for circulating a carrier fluid comprising a plurality of chambers maintained at different temperatures, each chamber comprising an inlet valve comprising an inlet pneumatic air pressure port for controlling inflow of the carrier fluid to the chamber; and an outlet valve comprising an outlet pneumatic air pressure port for controlling outflow of the carrier fluid from the chamber; wherein the chambers are sequentially connected such that the outlet valve of one chamber of the chambers is connected to the inlet valve of an adjacent chamber of the chambers in a direction of the carrier fluid flow.

In another aspect of the present invention, there is provided a method for operating the above apparatus for circulating a carrier fluid, which comprises simultaneously applying a pressure to an inlet pneumatic air pressure port of a chamber and venting an outlet pneumatic air pressure port of an adjacent chamber in a fluid flow direction; allowing the carrier fluid to move from the one chamber to the adjacent chamber; controlling a pressure applied to the outlet pneumatic air pressure port of the adjacent chamber to retain the carrier fluid in the adjacent chamber for a predetermined time; and repeating the applying and controlling to circulate the carrier fluid.

In still another aspect of the present invention, there is provided an apparatus for amplifying an amount of a nucleic acid contained in a sample using a polymerase chain reaction, comprising three chambers, each chamber comprising an inlet valve comprising a pneumatic air pressure port for controlling inflow of the carrier fluid to the chamber; and an outlet valve comprising a pneumatic air pressure port for controlling outflow of the carrier fluid from the chamber; wherein the chambers are sequentially connected such that the outlet valve of one chamber of the chambers is connected to the inlet valve of an adjacent chamber of the chambers in a direction that the fluid flows; and wherein the three chambers comprise a first chamber maintained at a temperature for denaturing, a second chamber maintained at a temperature for annealing, and a third chamber maintained at a temperature for extension.

In still another aspect of the present invention, there is provided an apparatus for amplifying an amount of a nucleic acid contained in a sample using a polymerase chain reaction, comprising two chambers, each chamber comprising an inlet valve comprising a pneumatic air pressure port for controlling inflow of the carrier fluid to the chamber; and an outlet valve comprising a pneumatic air pressure port for controlling outflow of the carrier fluid from the chamber; wherein the outlet valve of a first chamber is connected to the inlet valve of a second chamber; and wherein the first chamber is maintained at a temperature for denaturing and the second chamber is maintained at a temperature for annealing and extension.

In still another aspect of the present invention, there is provided an apparatus for circulating a carrier fluid, comprising a micro-channel comprising a first section for retaining a sample fluid and at least one second section for retaining a magnetic fluid, the sections being maintained at different temperatures; a valve connected to the micro-channel; and a magnet disposed on the micro-channel, for generating a magnetic field to move the magnetic fluid.

In still another aspect of the present invention, there is provided a method for operating the above apparatus for circulating a carrier fluid, which comprises applying a power to the magnet to move the magnetic fluid, thereby moving the carrier fluid toward an adjacent second section of the at least one second section.

In still another aspect of the present invention, there is provided an apparatus for amplifying an amount of a nucleic acid contained in a sample using a polymerase chain reaction, the apparatus comprising a micro-channel comprising a first section for retaining a sample fluid and two second sections for retaining a magnetic fluid; a valve connected to the micro-channel; and a magnet disposed on the micro-channel, for generating a magnetic field to move the magnetic fluid, wherein the first section is maintained at a temperature for denaturing, the two second sections are maintained at temperatures for annealing and extension.

In still another aspect of the present invention, there is provided an apparatus for amplifying an amount of a nucleic acid contained in a sample using a polymerase chain reaction, the apparatus comprising a micro-channel comprising a first section for retaining a sample fluid and a second section for retaining a magnetic fluid; an inlet/outlet valve connected to the micro-channel; and a magnet disposed on the micro-channel, for generating a magnetic field to move the magnetic fluid, wherein the first section is maintained at a temperature for denaturing and the second section is maintained at a temperature for annealing and extension.

In still another aspect of the present invention, there is provided a chip comprising a substrate, one of the above apparatus for amplifying a nucleic acid disposed on the substrate and an electrophoresis means operatively-interconnected with the apparatus.

BRIEF DESCRIPTION OF THE DRAWINGS

The above object and advantages of the present invention will become more apparent by describing in detail preferred embodiments thereof with reference to the attached drawings in which.

DETAILED DESCRIPTION OF THE INVENTION

Figure 1:
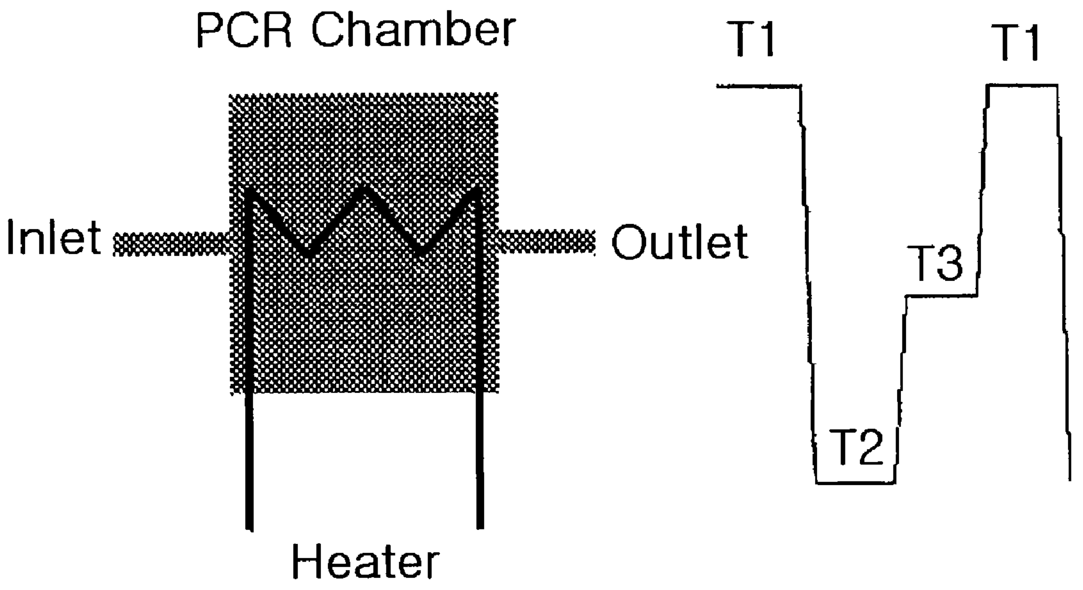
Fig. 1 (Prior Art)
FIG. 1 illustrates a conventional PCR system.
Figure 2:
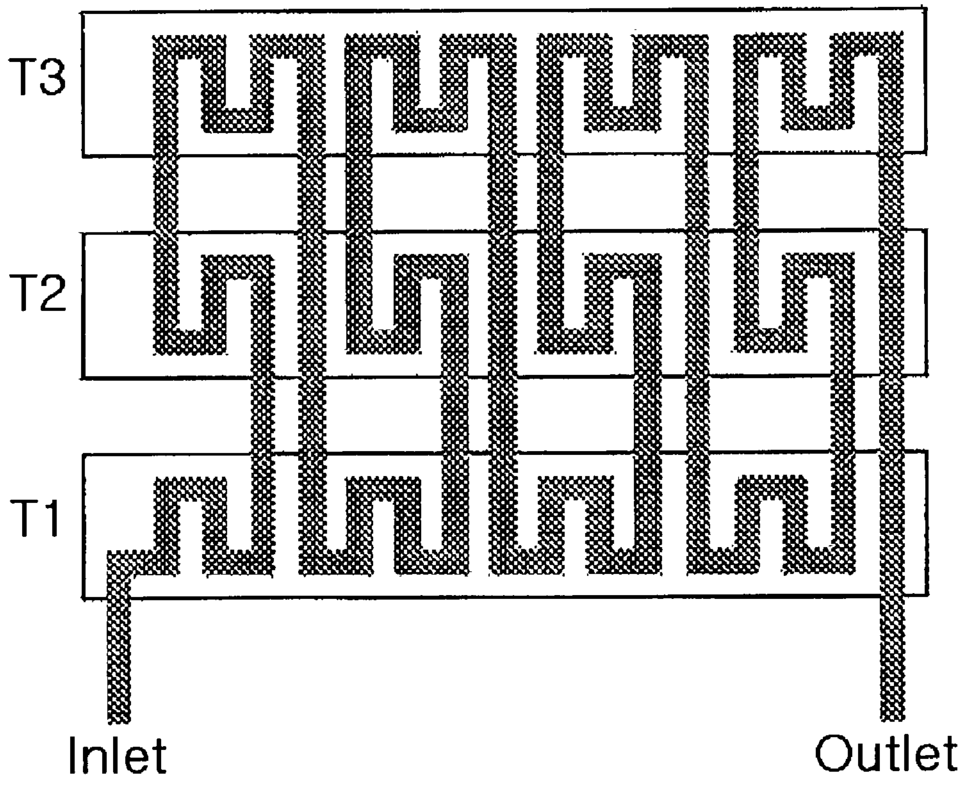
Fig. 2 (Prior Art)
FIG. 2 illustrates another form of a conventional PCR system.
Figure 3:
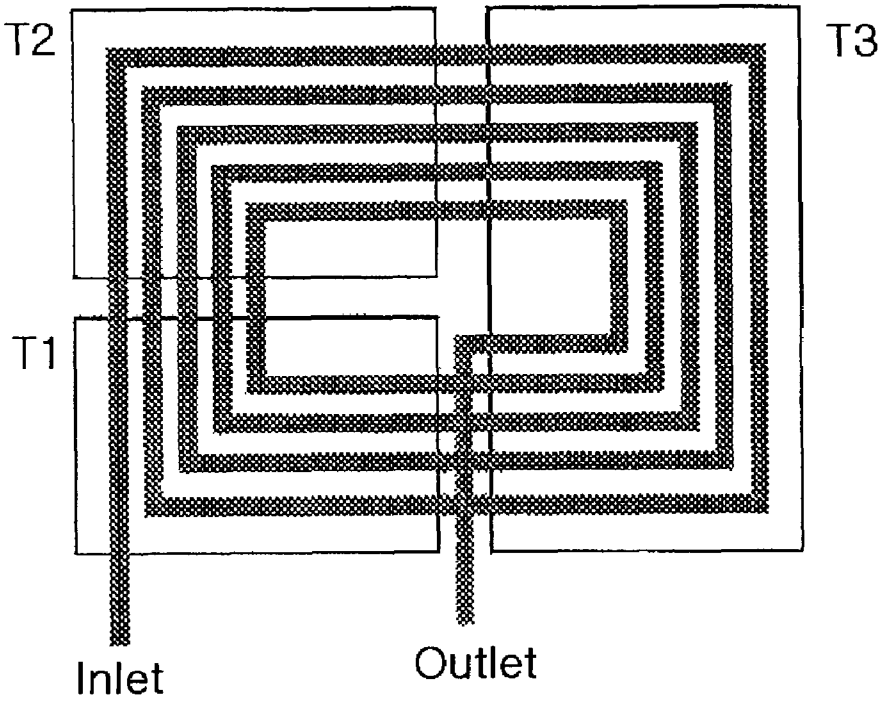
Fig. 3 (Prior Art)
FIG. 3 illustrates still another form of a conventional PCR system.

The apparatus of the present invention includes two or more chambers maintained at different temperatures, through which a carrier fluid circulates. That is, the apparatus for circulating a carrier fluid includes two or more chambers maintained at different temperatures, each chamber comprising an inlet valve comprising a pneumatic air pressure port for controlling inflow of the carrier fluid to the chamber (inlet pneumatic air pressure port); and an outlet valve comprising a pneumatic air pressure for controlling outflow of the carrier fluid from the chamber (outlet pneumatic air pressure port); wherein the chambers are sequentially connected such that the outlet valve of one chamber is connected to the inlet valve of an adjacent chamber in a direction of the fluid flow.

A carrier fluid includes any fluid to be retained in a temperature-maintained zone for reaction for a predetermined time. The carrier fluid may include a biochemical fluid, such as a fluid for polymerase chain reaction comprising a template DNA, an oligonucleotide primer, dNTP [deoxyadenosine triphosphate (dATP), deoxycytidine triphosphate (dCTP), deoxyguanidine triphosphate (dGTP), deoxythymidine triphosphate (dTTP)], and a thermostable DNA polymerase.

In an apparatus for circulating a carrier fluid of the present invention, the outlet valve of each chamber may be integrated with the inlet valve of a subsequent chamber such that the chambers are fluidly connected.

Both the inlet valve and the outlet valve may be a passively operated valve. Further, the passively operating valve may be a valve where a channel of an outlet valve is formed to be narrower than that of an inlet valve or a valve where an inner surface of an outlet valve is treated with a hydrophobic material to control flow of a carrier fluid.

In an apparatus of the present invention, the carrier fluid is circulated by controlling a pressure applied to each chamber. The method for operating an apparatus for circulating a carrier fluid comprises applying a pressure to the inlet pneumatic air pressure port of a chamber and venting an outlet pneumatic air pressure port of an adjacent chamber in a fluid flow direction at the same time to allow the carrier fluid to move from the chamber to the adjacent chamber; controlling a pressure applied to the outlet pneumatic air pressure port of the adjacent chamber to retain the carrier fluid in the adjacent chamber for a predetermined time; and repeating the applying and controlling steps in turn to circulate the carrier fluid.

The carrier fluid may be introduced and discharged through the inlet and outlet pneumatic air pressure port of a chamber, respectively.

The present invention also includes, within its scope, an apparatus for amplifying a nucleic acid using a carrier fluid circulating apparatus. The amplifying apparatus is used in amplifying an amount of a nucleic acid present in a sample using a polymerase chain reaction and may comprise three chambers. Each chamber comprises an inlet valve comprising a pneumatic air pressure port for controlling inflow of the carrier fluid to the chamber and an outlet valve comprising a pneumatic air pressure for controlling outflow of the carrier fluid from the chamber. The chambers are sequentially connected such that the outlet valve of one chamber is connected to the inlet valve of an adjacent chamber in a direction the fluid flows. The three chambers include a first chamber maintained at a temperature for denaturing, a second chamber maintained at a temperature for annealing, and a third chamber maintained at a temperature for extension.

Further, the amplifying apparatus is used in amplifying an amount of a nucleic acid present in a sample using a polymerase chain reaction and may comprise two chambers. Each chamber comprises an inlet valve comprising a pneumatic air pressure port for controlling inflow of the carrier fluid to the chamber and an outlet valve comprising a pneumatic air pressure for controlling outflow of the carrier fluid from the chamber. The outlet valve of one chamber is connected to the inlet valve of the other chamber. One chamber is maintained at a temperature for denaturing and the other chamber is maintained at a temperature for both annealing and extension.

An apparatus for amplifying a nucleic acid of the present invention may be a miniaturized circular PCR cycler, in which a biochemical fluid, such as a PCR fluid, circulates along two or three chambers maintained at different temperatures. For example, one cycle of DNA amplification may be completed by circulating a sample fluid along a first chamber (maintained at a temperature for denaturing, T1)→a second chamber (maintained at a temperature for annealing, T2)→a third chamber (maintained at a temperature for extension, T3)→or by circulating a sample fluid along a first chamber (maintained at a temperature for denaturing, T1)→a second chamber (maintained at a temperature for both annealing and extension, T2'). By performing a plurality of cycles in the PCR apparatus, an amount of DNA in a sample is exponentially amplified.

Alternatively, two or more sections maintained at different temperatures may be formed in a micro-channel. That is, an apparatus for circulating a carrier fluid comprises a micro-channel having two or more sections maintained at different temperatures. One section retains a sample fluid and the remaining one or more sections retain a magnetic fluid. An inlet/outlet valve is connected to the micro-channel and a magnet is disposed outside the micro-channel for forming a magnetic field to effect on the magnetic fluid.

The magnet may be a magnet located in a center of the micro-channel or an electromagnet located along the micro-channel.

The magnetic fluid includes any fluid to be moved by a magnetic force of a simple magnet or an electromagnet. For example, the magnetic fluid may be a mixture of a ferromagnetic particle in an aqueous medium (an aqueous-based ferrofluid), in an oil (an oil-based ferrofluid), or in a polymeric gel (a polymeric gel-based ferrofluid). Among them, an oil-based ferrofluid is preferred.

A magnetic power or an electric power is applied to the magnet to cause a movement thereof. As the magnet moves, the magnetic fluid moves, which allows the carrier fluid to move toward an adjacent section.

Where the micro-channel includes three sections, there is provided an apparatus for amplifying an amount of a nucleic acid present in a sample using a polymerase chain reaction. The three sections include a first section maintained at a temperature for denaturing, a second section maintained at a temperature for annealing, and a third section maintained at a temperature for extension.

Where the micro-channel includes two sections, there is also provided an apparatus for amplifying an amount of a nucleic acid present in a sample using a polymerase chain reaction. One section is maintained at a temperature for denaturing and the other section is maintained at a temperature for both annealing and extension.

An apparatus for amplifying a nucleic acid of the present invention may be a miniaturized circular PCR cycler, in which a biochemical fluid, such as a PCR fluid, circulates along two or three sections maintained at different temperatures of micro-channel. For example, one cycle of DNA amplification may be completed by sequentially circulating a carrier fluid along a first section (maintained at a temperature for denaturing, T1)→a second section (maintained at a temperature for annealing, T2)→a third section (maintained at a temperature for extension, T3) or by circulating a carrier fluid along a first section (maintained at a temperature for denaturing, T1)→a second section (maintained at a temperature for both annealing and extension, T2'). By performing a plurality of cycles in the PCR apparatus, an amount of DNA in a sample is exponentially amplified.

The amplifying apparatus can be implemented in a chip. The chip comprises a substrate, an apparatus for amplifying a nucleic acid disposed on the substrate and an electrophoresis means operatively linked to the apparatus. And, the substrate may comprise a heating means deposited thereon. The heating means includes a thermoelectric device, an infrared light, or a pre-heated metal block.

For example, an amount of DNA in the sample introduced to the chip of the present invention is amplified. And then, the amplified DNA is supplied to an electrophoresis means to be isolated according to a molecular weight or a charge thereof and finally identified as a specific DNA. The substrate of the chip may be selected from the group consisting of glass, quartz, silicon, plastic, ceramic, and metal. The electrophoresis means may be a multi-channel form for capillary electrophoresis. The apparatus for PCR amplification and the electrophoresis means may be embodied on a substrate using a photolithography technique.

The present invention is described in more detail referring to the attached drawings hereinafter.

Figure 4:
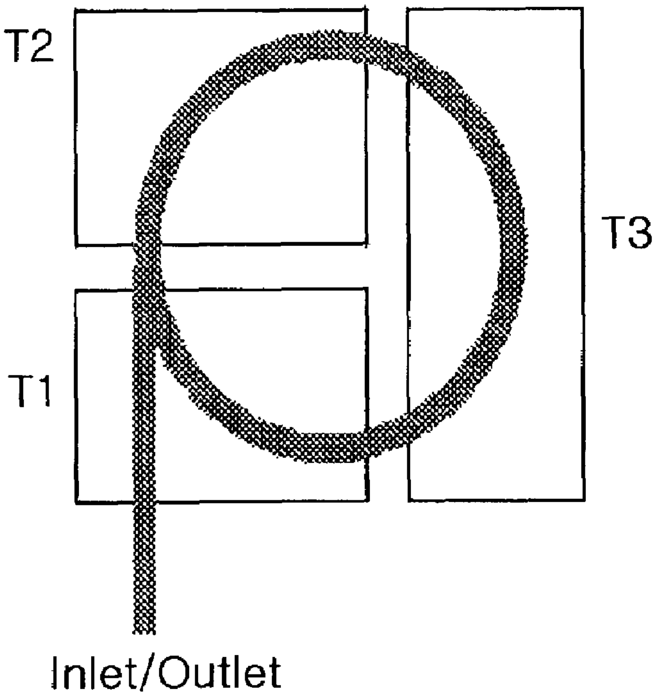
FIGS. 4 and 5 illustrate a schematic view where a biochemical fluid, such as a PCR fluid, is circulated through two or more sections maintained at different temperatures for PCR.
Figure 5:
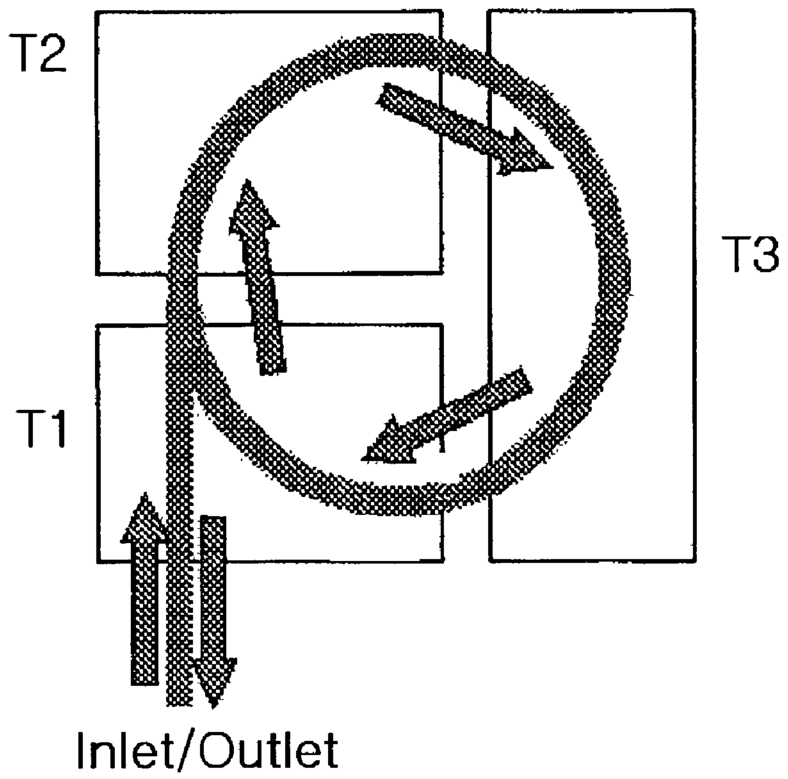

As shown in FIGS. 4 and 5, a biochemical fluid, such as a PCR fluid, is circulated along two or more sections maintained at different temperatures for PCR. In FIGS. 4 and 5, a circle shows a channel to circulate a carrier fluid and T1, T2, and T3 show different temperature zones, respectively. The arrow shows a direction to circulate or introduce/discharge a carrier fluid. According to the present invention, there is no need for a long channel and/or a complicated circuit for the accurate control of temperatures as required in conventional systems.

Figure 6:
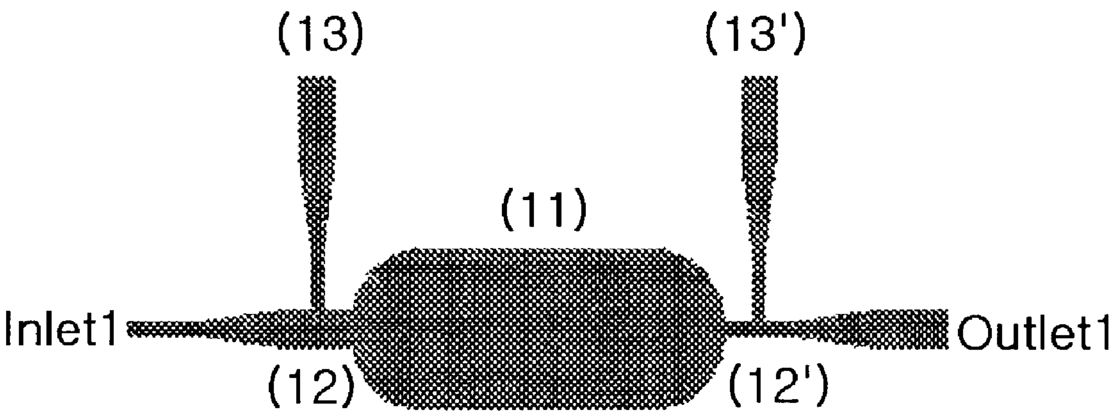
FIGS. 6 and 7 illustrate basic components of each chamber unit in a pneumatic air pressure type of PCR system.
Figure 7:
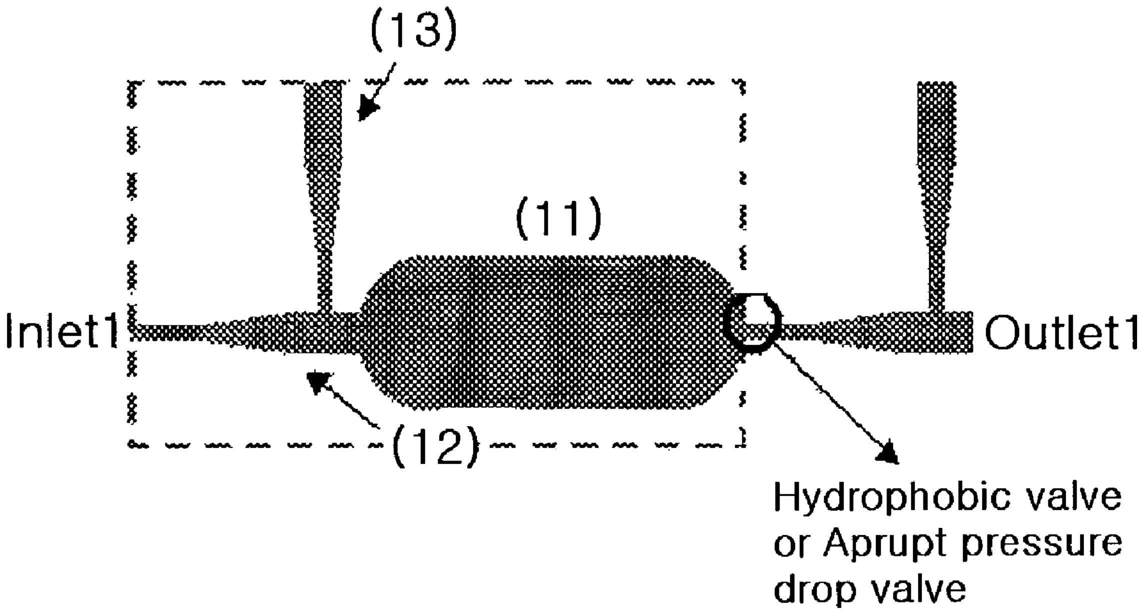

FIGS. 6 and 7 illustrate components of each chamber unit in a pneumatic air pressure type of PCR system. In FIGS. 6 and 7, a temperature-maintained chamber (or micro-chamber) (11) retains a carrier fluid for polymerase chain reaction for a predetermined time. The chamber unit includes a chamber (11), an inlet valve (12) comprising a pneumatic air pressure port (13), an outlet valve (12') comprising a pneumatic air pressure port (13'). The chamber units may be interconnected to form an apparatus where the outlet valve of each chamber may be integrated with the inlet valve of a subsequent chamber. A flow of the carrier fluid is controlled by a passively operated valve, such as an abrupt pressure drop valve where a channel of the outlet valve is formed to be narrower than that of the inlet valve, thereby giving an abrupt pressure drop effect, or a hydrophobic valve where an inner surface of the outlet valve is treated with a hydrophobic material to control flow of the carrier fluid.

Where a higher pressure is applied to the inlet pneumatic air pressure port (13) in the inlet valve (12) than the outlet pneumatic air pressure port (13') in the outlet valve (12'), the carrier fluid in the chamber (11) moves toward the outlet valve (12'). At that time, by lowering the air pressure applied to the outlet pneumatic air pressure port (13'), the air may be discharged.

Those components of each chamber unit make the carrier fluid flow in one direction by employing a pneumatic air pressure. Two or more chamber units may be interconnected to form an apparatus for circulating the carrier fluid by a pneumatic air pressure.

Figure 8:
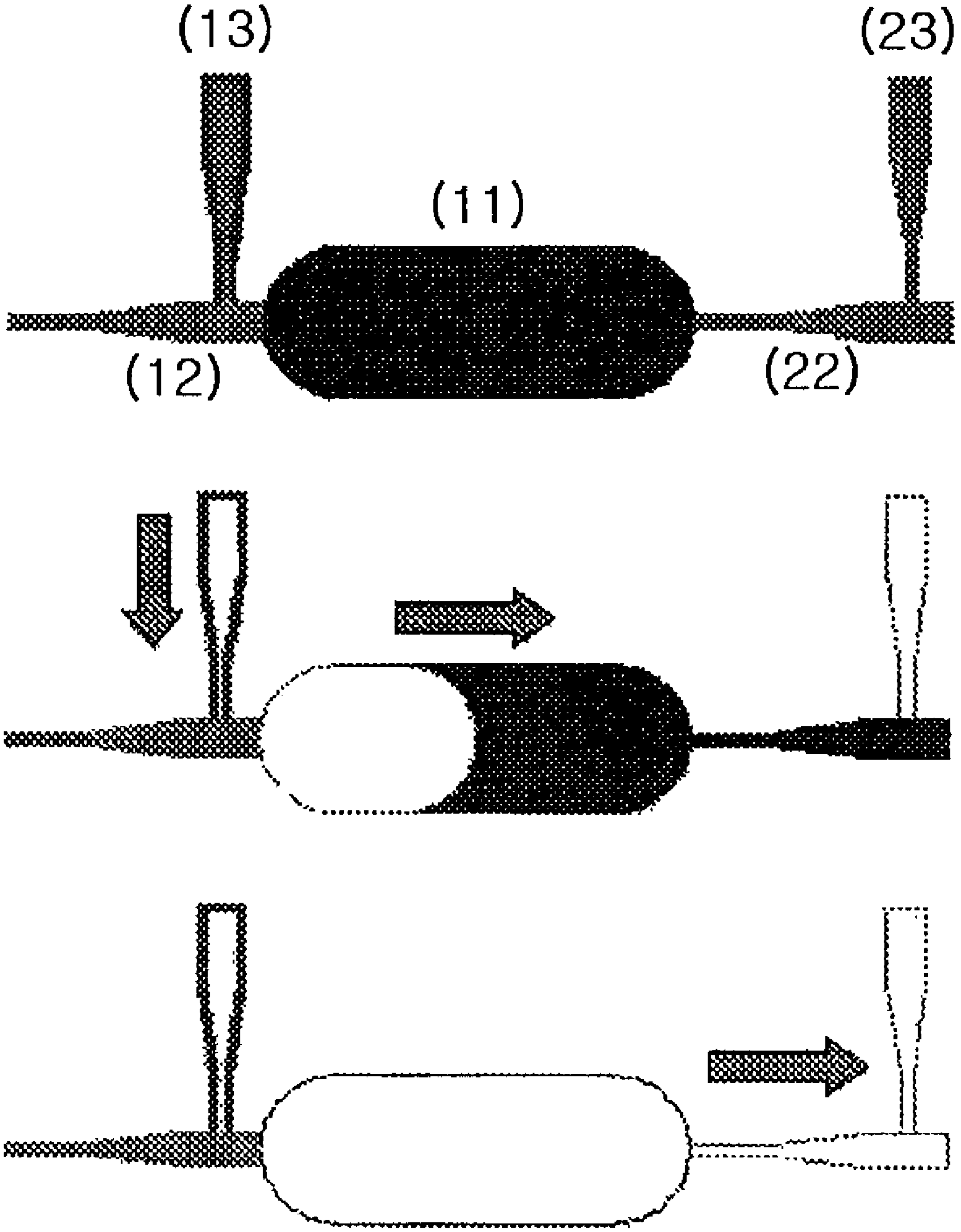
FIG. 8 schematically illustrates a principle of operation in an apparatus having one chamber.

FIG. 8 schematically illustrates a principle of operation in an apparatus having one chamber. A carrier fluid in a chamber (11) moves to an outlet by an air pressure applied to the inlet pneumatic air pressure port (13). Where the air pressure applied to the inlet pneumatic air pressure port (13) is higher than the air pressure applied to an outlet valve (22), the carrier fluid moves toward the outlet valve (22). A hydrophobic treatment or an abrupt pressure drop due to a narrower channel structure may passively operate the outlet valve (22).

Figure 9:
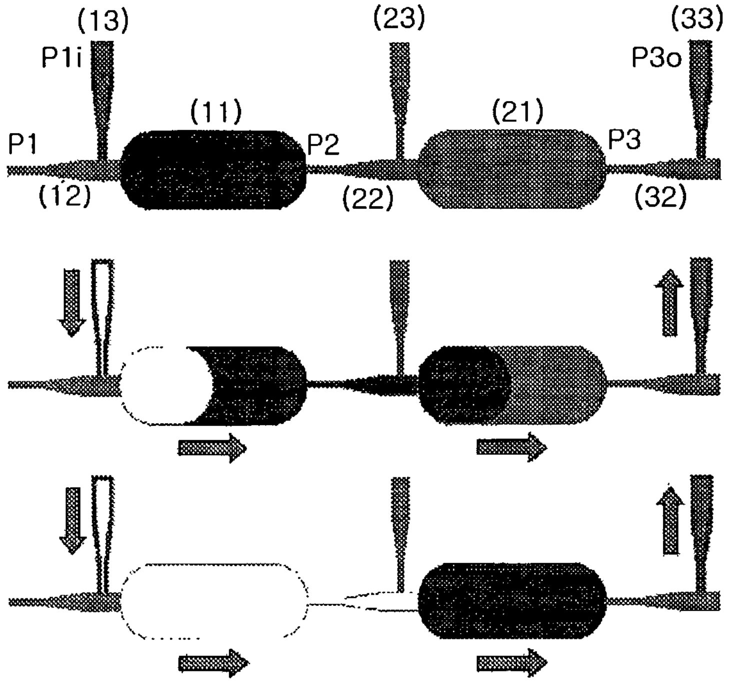
FIGS. 9 and 10 schematically illustrate a principle of operation in an apparatus having two or three interconnected chamber units, respectively.

FIG. 9 schematically illustrates a principle of operation in an apparatus having two chamber units interconnected. Applying an air pressure to an inlet pneumatic air pressure port (13) of a first chamber 11 and venting an outlet pneumatic air pressure port (33) of a second chamber 21 cause a pressure difference (P1*i*-P30) between the chamber 11 and 21. Where the air pressure (P1*i*) of the inlet pneumatic air pressure port (13) is higher than the air pressure (P2) of a valve (22), the carrier fluid in the first chamber (11) moves toward the second chamber (21). Further, where the air pressure (P3) of a valve (32) is higher than the air pressure (P1*i*) of a valve (12), the carrier fluid is retained in the second chamber (21) while air is easily discharged.

Figure 10:
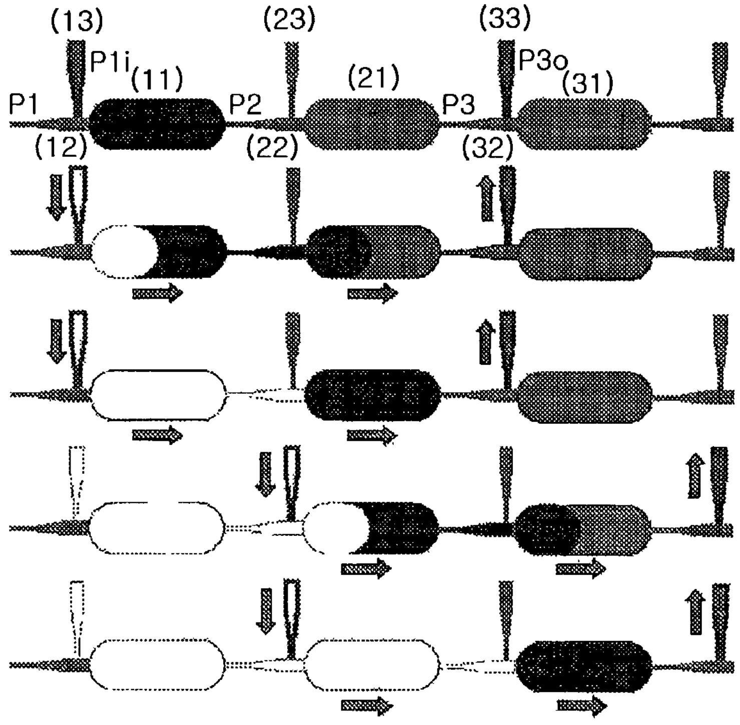

FIG. 10 schematically illustrates a principle of operation in an apparatus having three chamber fluidly interconnected units. This is operated in accordance with the same process as described referring to FIG. 9. Applying an air pressure successively to pneumatic air pressure ports (13, 23, and 33) makes a carrier fluid successively move through the chambers (11, 21, and 31).

Figure 11:
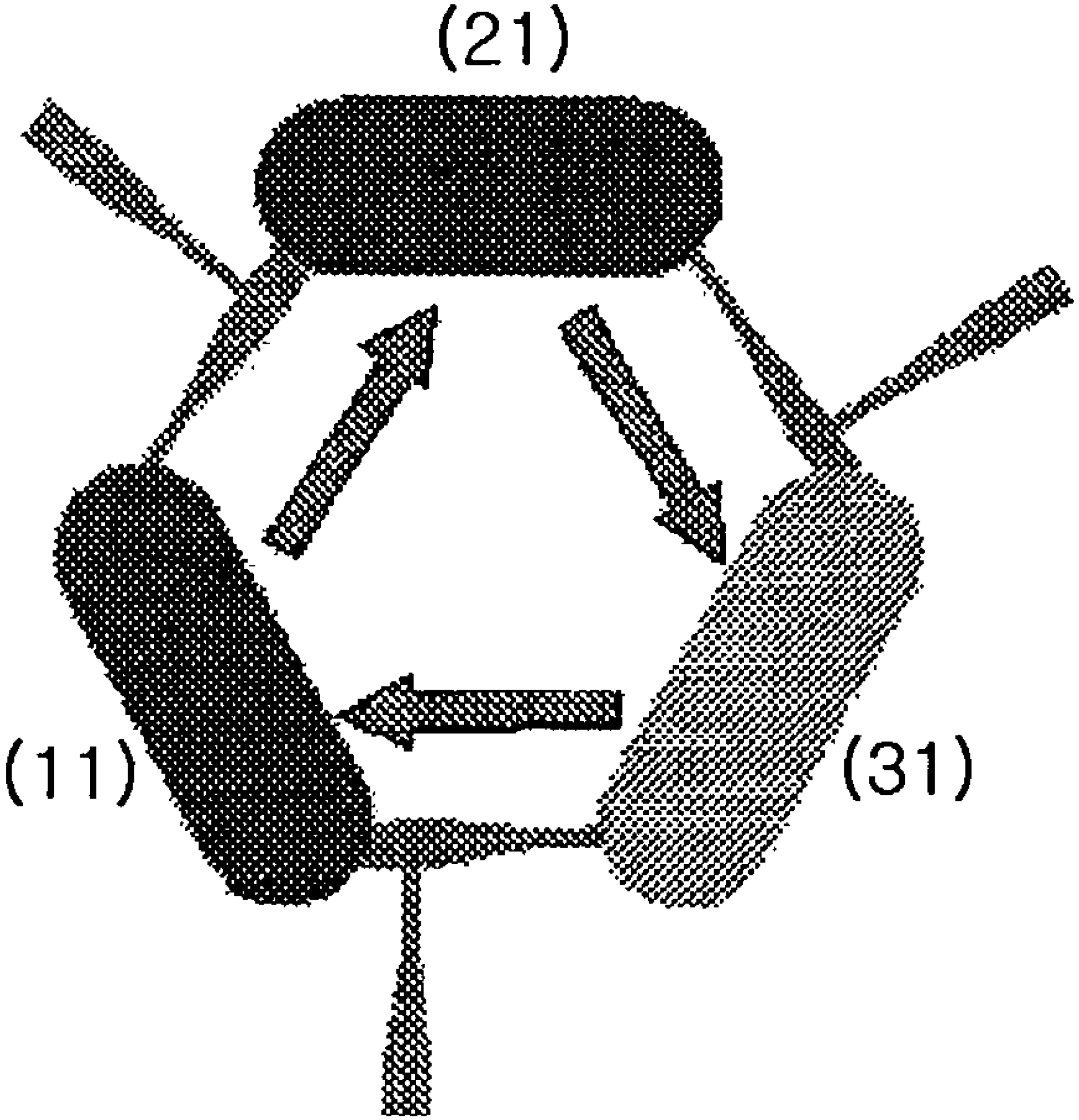
FIG. 11 illustrates a schematic view of an apparatus for circulating a carrier fluid having three interconnected chambers.

FIG. 11 illustrates a schematic view of an apparatus for circulating a carrier fluid having three interconnected chambers. The principle of operation is the same as described referring to FIG. 10. That is, applying an air pressure successively to pneumatic air pressure ports makes a carrier fluid successively moved through a first chamber (11) (Temp Zone 1), a second chamber (21) (Temp Zone 2), and a third chamber (31) (Temp Zone 3) according to the arrow direction.

Figure 12:
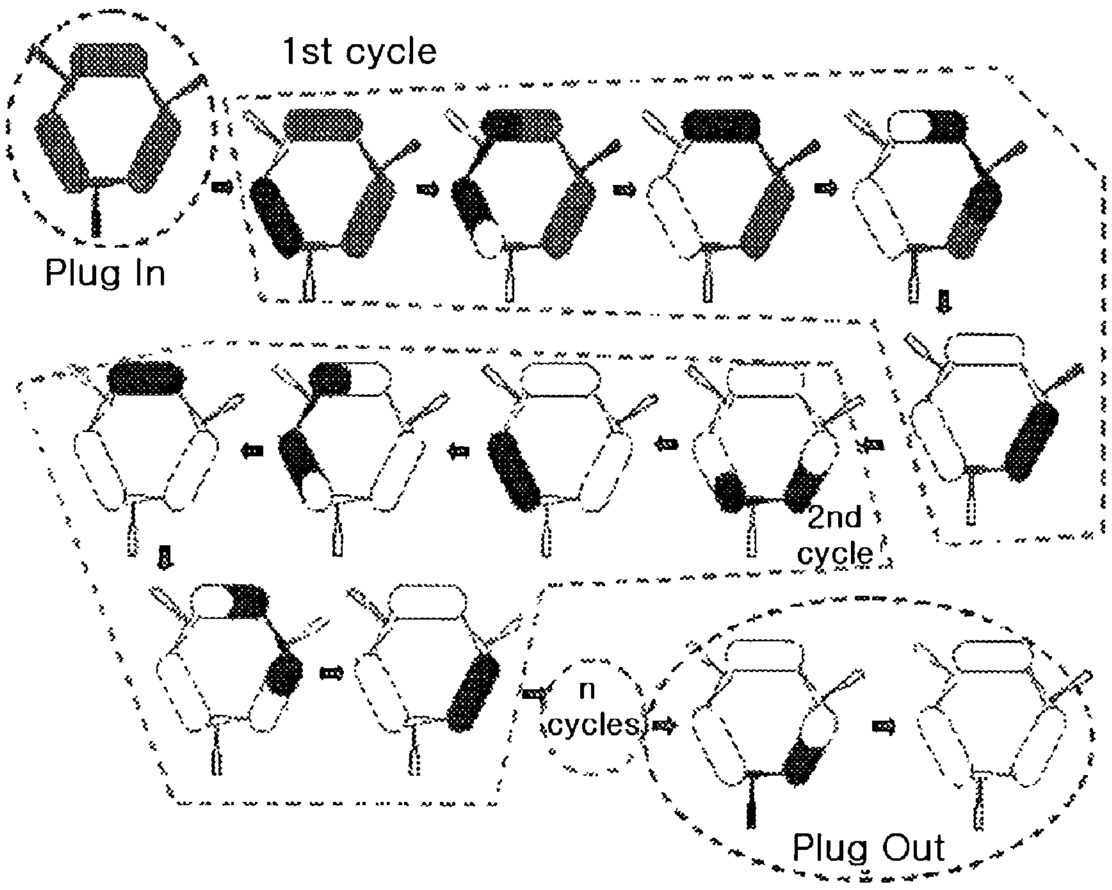
FIG. 12 schematically illustrates a principle of operation in an apparatus for circular PCR.

FIG. 12 schematically illustrates a principle of operation in an circular PCR apparatus. A carrier fluid is introduced, via a plug, to a chamber (11). During a first cycle, the introduced carrier fluid is circulated through the chambers (denaturing chamber (11)→annealing chamber (21)→extension chamber (31)) to be subjected to polymerase chain reaction. In the same way, a second PCR cycle is performed. The repetition of the cycle causes the desired number of polymerase chain reactions as desired. After a predetermined number of cycles, the carrier fluid is discharged through the plug to move to a channel or a chamber for analysis, such as electrophoresis.

Figure 13:
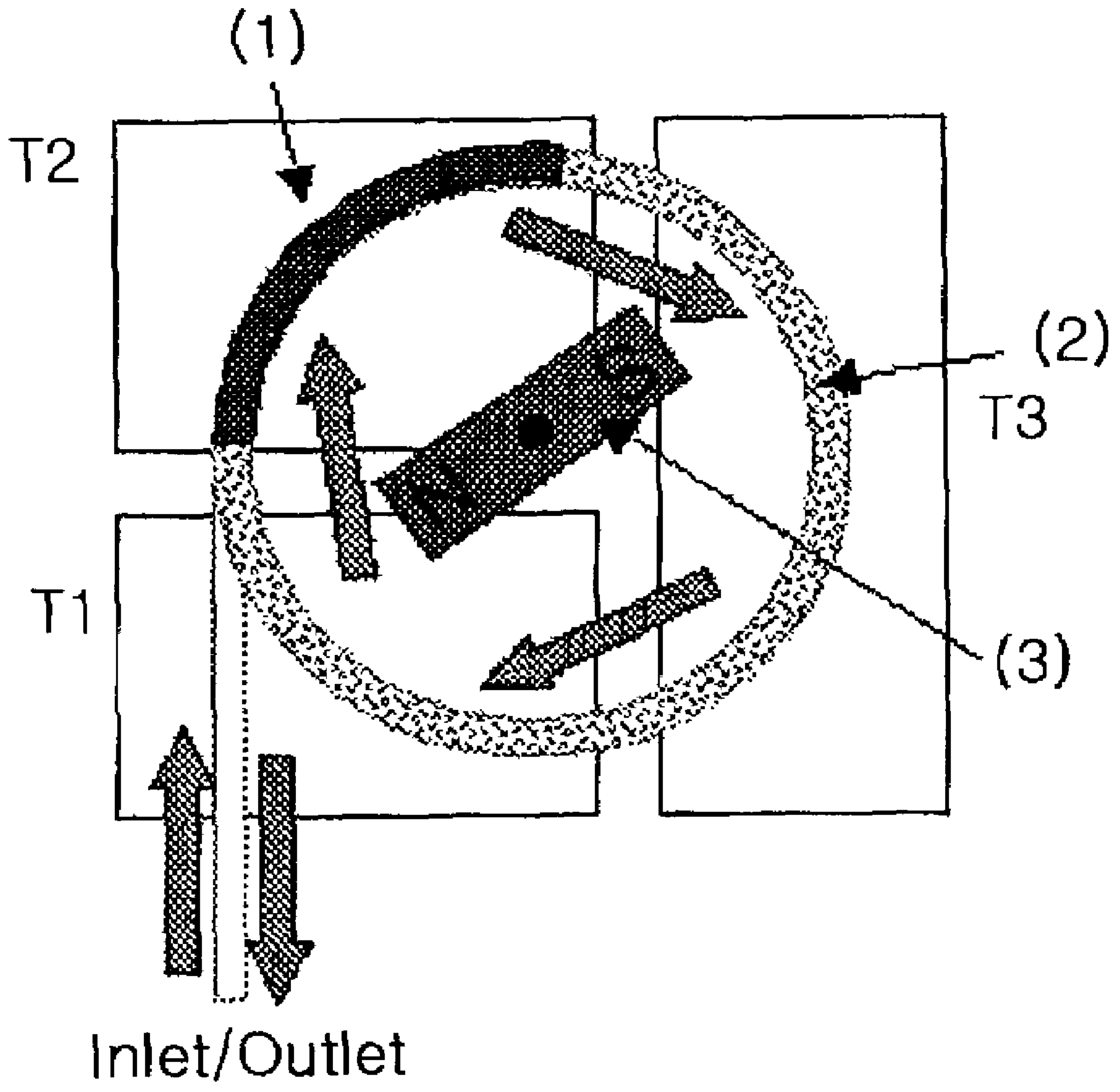
FIG. 13 schematically illustrates a principle of operation for circulating a biochemical fluid, such as a PCR fluid, using a magnetic fluid in a magnetic fluid type of PCR system.

FIG. 13 schematically illustrates a principle of operation for circulating a biochemical fluid, including a PCR fluid, using a magnetic fluid in a magnetic fluid type of PCR system. This apparatus uses a magnetic fluid, in place of pneumatic air pressure, for circulating a biochemical fluid. A biochemical fluid (1) is circulated along the sections maintained at different temperatures (T1, T2, T3), by moving a magnetic fluid (2) along the micro-channel, which is successively operated by a magnet (3) located in the center of the micro-channel or an electromagnet located along the micro-channel.

Further understanding of the nature and advantages of the present invention herein may be realized by reference to the following Examples. The following Examples are given for the purpose of illustration only, and are not intended to limit the scope of the present invention.

EXAMPLE 1

Pneumatic Air Pressure Type of PCR System having Two Chamber Units

The apparatus, for amplifying an amount of a nucleic acid present in a sample using a polymerase chain reaction, had two chambers. Each chamber had an inlet valve comprising a pneumatic air pressure port for controlling inflow of the carrier fluid to the chamber and an outlet valve comprising a pneumatic air pressure for controlling outflow of the carrier fluid from the chamber. The outlet valve of one chamber was integrated with the inlet valve of the other chamber. One chamber was maintained at about 94° C. for denaturing, the other chamber was maintained at about 68° C. for both annealing and extension. The amount of a nucleic acid present in a sample was amplified by polymerase chain reaction.

EXAMPLE 2

Pneumatic Air Pressure Type of PCR System having Three Chamber Units

The apparatus, for amplifying an amount of a nucleic acid present in a sample using a polymerase chain reaction, had three chambers. Each chamber had an inlet valve comprising a pneumatic air pressure port for controlling inflow of the carrier fluid to the chamber and an outlet valve comprising a pneumatic air pressure for controlling outflow of the carrier fluid from the chamber. The chambers were sequentially connected such that the outlet valve of one chamber was integrated with the inlet valve of an adjacent chamber in a direction the fluid flows. The three chambers included a first chamber maintained at about 94° C. for denaturing, a second chamber maintained at about 55° C. for annealing, and a third chamber maintained at about 72° C. for extension. The amount of a nucleic acid present in a sample was amplified by polymerase chain reaction.

EXAMPLE 3

Magnetic Fluid Type of PCR System having a Micro-Channel with Two Sections

The apparatus for amplifying an amount of a nucleic acid in a sample, using a polymerase chain reaction, had a micro-channel having two sections. One section retained a sample fluid and the other section retained a magnetic fluid. An inlet/outlet valve was connected to the micro-channel and a magnetic stirrer was located in the center of the micro-channel. One section was maintained at about 94° C. for denaturing and the other section was maintained at about 68° C. for both annealing and extension. The amount of a nucleic acid present in a sample was amplified by polymerase chain reaction.

EXAMPLE 4

Magnetic Fluid Type of PCR System having a Micro-Channel with Three Sections The apparatus for amplifying an amount of a nucleic acid in a sample, using a polymerase chain reaction, had a micro-channel having three sections. One section retained a sample fluid and the remaining two sections retained a magnetic fluid. A valve was connected to the micro-channel and a magnetic stirrer was located in the center of the micro-channel. The three sections included a first section maintained at about 94° C. for denaturing, a second section maintained at about 55° C. for annealing, and a third section maintained at about 72° C. for extension. The amount of a nucleic acid contained in a sample was amplified by polymerase chain reaction.

The apparatus and method for circulating a carrier fluid according to the present invention have following advantages.

In a conventional PCR cycler, heating (usually 1-2 seconds) and cooling (usually 3-4 seconds) processes are required. In the present invention, temperature preset chambers are used and a sample fluid goes through a series of such chambers. Thus, a predetermined time is taken for the sample fluid to move from one chamber to another chamber. The moving time depends on a pneumatic air pressure or a magnetic force and is less than about 1 second. Thus, the duration of one cycle is greatly reduced compared with a conventional PCR cycler.

Further, a carrier fluid moves along temperature-maintained chambers or sections, which makes it possible to control PCR conditions according to characteristics of a biochemical fluid by varying a residence time of the carrier fluid in each of the chambers or sections.

And, there is no need for a complicated circuit. In a conventional PCR cycler, complicated circuits, such as PID (proportional/integral/differential), are needed for an accurate control of temperatures. Further, a high voltage for a rapid heating causes an overshoot effect, thereby increasing a temperature of a chamber, e.g., by about 1° C. to 2° C.

There is no need for a cooling system. In a conventional PCR cycler, a cooling fan or a thermoelectric apparatus is required for rapid cooling. However, in the present invention, there is no need for any circuits for cooling or cooling system.

There is no need for an extraordinarily long channel as in a continuous-flow PCR cycler. Therefore, it is possible to manufacture portable system as well as to reduce the size of the entire system of the present invention.

The present invention may be embodied on a microchip, such as lab-on-a-chip, which makes it possible to use a photolithography technique with silicon, glass, or plastic, etc.

The present invention may be embodied on a microchip, which makes it possible to use a small amount (mL to pL) of a biochemical fluid, such as a PCR fluid.

This application is based. upon and claims priority from Korean Patent Application No. 2001-69955 filed Nov. 10, 2001, the contents of which are incorporated herein by reference.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An apparatus for circulating a carrier fluid comprising:
- a plurality of chambers maintained at different temperatures, each chamber comprising:
  - an inlet valve comprising an inlet channel connected to the chamber, and an inlet pneumatic air pressure port connected directly with the inlet channel for controlling inflow of the carrier fluid to the chamber; and
  - an outlet valve comprising an outlet channel connected to the chamber, and an outlet pneumatic air pressure port connected directly with the outlet channel for controlling outflow of the carrier fluid from the chamber;
- wherein the chambers are sequentially connected such that the outlet valve of one chamber of the plurality of chambers substitutes for the inlet valve of a next chamber of the plurality of chambers in a direction of the carrier fluid flow and form a closed loop.

2. The apparatus for circulating a carrier fluid of claim 1, wherein the outlet valve of each chamber is integrated with the inlet valve of the adjacent chamber.

3. The apparatus for circulating a carrier fluid of claim 1, wherein the inlet valve and the outlet valve each comprise a passively operated valve.

4. The apparatus for circulating a carrier fluid of claim 3, wherein the passively operated outlet valve comprises a channel narrower than a channel of the passively operated inlet valve.

5. The apparatus for circulating a carrier fluid of claim 1,
- wherein the apparatus amplifies an amount of a nucleic acid contained in a sample using a polymerase chain reaction; and
- wherein the chambers comprise a first chamber maintained at a temperature for denaturing, a second chamber maintained at a temperature for annealing, and a third chamber maintained at a temperature for extension.

6. The apparatus for circulating a carrier fluid of claim 1,
- wherein the apparatus amplifies an amount of a nucleic acid contained in a sample using a polymerase chain reaction; and
- wherein the chambers comprise a first chamber maintained at a temperature for denaturing and a second chamber maintained at a temperature for annealing and extension.

7. The apparatus for circulating a carrier fluid of claim 1, further comprising:
- an electrophoresis means operatively linked to the apparatus, wherein the apparatus and the electrophoresis means are disposed on a substrate forming a chip.

8. The apparatus of claim 7, wherein the substrate comprises a glass, a quartz, a silicon, a plastic, a ceramic, a metal, or a composition comprising one or more of the foregoing materials.

9. The apparatus of claim 7, wherein the substrate comprises a heating means deposited thereon.

10. The apparatus of claim 9, wherein the heating means comprises a thermoelectric device, an infrared light, or a pre-heated metal block.

11. The apparatus for circulating a carrier fluid of claim 3, wherein an inner surface of the outlet valve comprises a hydrophobic material.

12. A method for operating an apparatus for circulating a carrier fluid comprising:
- simultaneously applying a pressure to an inlet pneumatic air pressure port of one chamber and venting an outlet pneumatic air pressure port of an adjacent chamber in a fluid flow direction to allow the carrier fluid to move from the one chamber to the adjacent chamber;
- controlling a pressure applied to the outlet pneumatic air pressure port of the adjacent chamber to retain the carrier fluid in the adjacent chamber for a predetermined time; and
- repeating the applying and the controlling, wherein the apparatus comprises:
  - a plurality of chambers maintained at different temperatures, each chamber comprising:
    - an inlet valve comprising an inlet channel connected to the chamber, and an inlet pneumatic air pressure port connected directly with the inlet channel for controlling inflow of the carrier fluid to the chamber; and
    - an outlet valve comprising an outlet channel connected to the chamber, and an outlet pneumatic air pressure port connected directly with the outlet channel for controlling outflow of the carrier fluid from the chamber;

wherein the chambers are sequentially connected such that the outlet valve of one chamber of the plurality of chambers substitutes for the inlet valve of a next chamber of the plurality of chambers in a direction of the carrier fluid flow and form a closed loop.

* * * * *